United States Patent [19]

Schwantje

[11] Plant 4,147

[45] Nov. 8, 1977

[54] AFRICAN VIOLET PLANT — PAULA

[75] Inventor: Werner Schwantje, Newark, Calif.

[73] Assignee: Sunnyside Nurseries, Inc., Hayward, Calif.

[21] Appl. No.: 756,116

[22] Filed: Jan. 3, 1977

[51] Int. Cl.[2] ..... A01H 5/00

[52] U.S. Cl. ..... Plt./69

[58] Field of Search ..... Plt./69

*Primary Examiner*—Robert E. Bagwill

*Attorney, Agent, or Firm*—James R. Cypher

[57] ABSTRACT

This invention relates to a new and distinct variety of African Violet plant named Paula which is a sport of "Rhapsodie" Type XVII-21 Red Star, named Mars, a commercial unpatented variety. This sport was selected from a flowering of Mars in commercial greenhouses in Hayward, Calif., because the color is distinctly different compared to Mars. The color is pink or dark rose compared to Mars. The color of Mars is Dogen Purpur 73/2 as designated by the "Dictionary of Color" by Maerz and Paul. The color of Paula is Red-Purple, Group 74-B, as designated by the color chart by R. F. Wilson, of the Royan Horticulture Society of London, England.

1 Drawing Figure

BACKGROUND OF THE INVENTION

The present new variety was discovered by me in a commercial nursery at Hayward, Calif. and repeated vegetations and flowerings of the sport by me through asexual reproduction show that the characteristics described come true to form and are established and transmitted through succeeding propagations. Commercial propagation of this new variety is now being carried on in Hayward, Calif., U.S.A. The new sport is different from Mars only in color.

These plants were grown under 75°–77° day temperature and 70°–72° night temperature.

BRIEF SUMMARY

The present new variety is a medium-large, compact plant with the inflorescence standing upright above the foliage. It has strength of stem, fast and vigorous growth which varies with light intensity, profuse flowering, uniform bouquet, prolonged blooming period with the older flowers fading slightly, resistance to disease, reliability in initiating new plantlets, retention of flowers past maturity on its stems and uniformity throughout its life cycle. The individual flowers are single, star-shaped with petals having ruffled margins and the color is Red-Purple, Group 74-B as designated by the color chart by R. F. Wilson of the Royal Horticulture Society of London, England. The color fades under high light intensity. The color is the principal feature that distinguishes it from the variety MARS.

DESCRIPTION OF THE PHOTOGRAPH

This new variety of African violet plant named Paula is illustrated by the accompanying photograph which shows the form and color characteristics of the plant and its blooms and foliage, the color rendition being as nearly true as is reasonably possible to obtain by conventional photographic procedures.

DETAILED DESCRIPTION

Plant:

*Name.*—Paula.

*Origin.*—Selected from commercial flowering.

*Height.*—10.16 cm to 15.24 cm tall.

*Growth.*—Compact, strong, vigorous, upright, uninterrupted, varies with light intensity.

*Size.*—Medium-large.

*Mutation prone.*—Very little.

Leaves:

*Shape.*—Round, medium-large, slightly serrated.

*Color.*—Upper side — dark green. Underside — reddish.

*Texture.*—Upperside — Medium hairy. Underside — Slightly hairy.

Petiole: Reddish, short, strong, slightly hairy.

Flowers:

*Number.*—8–14 per peduncle.

*Size.*—4–4.5 cm diameter each flower.

*Color.*—Red-Purple, Group 74-B from R.H.S. Color Chart.

*Peduncles.*—Reddish, short, strong.

*Inflorescence.*—Upright above foliage.

*Type.*—Single, star.

*Petals.*—5 to 7 per individual flower with ruffled margins.

Anthers: Light yellow, 3 to 5, very large and visible.

Ovary: Does not push through.

Other characteristics: Very long flowering period. Flowers will not drop. Older flowers fade slightly. Color fades under high light intensity.

I claim:

1. A new and distinct variety of African Violet as described and illustrated.

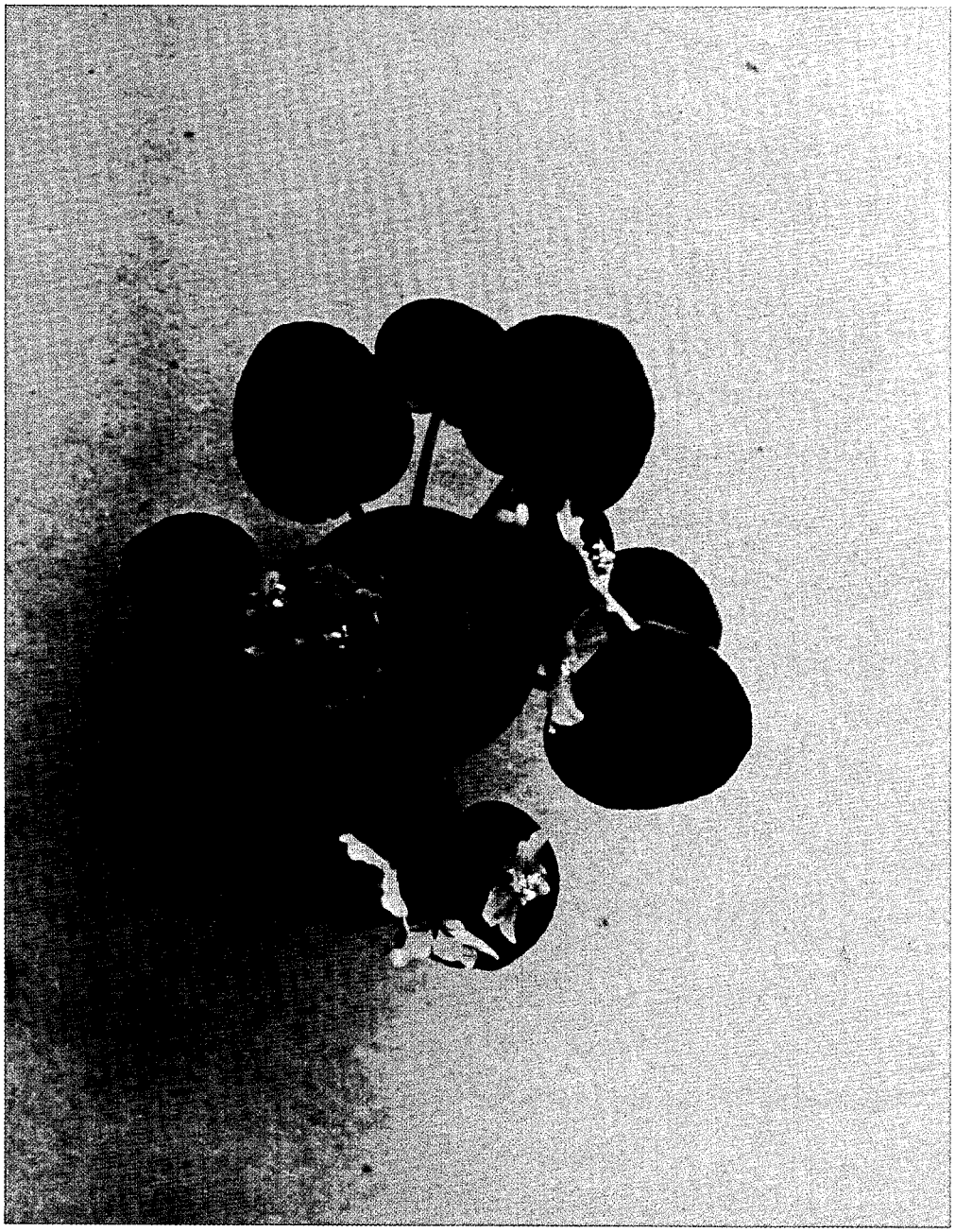

* * * * *